United States Patent [19]

DeLuca et al.

[11] Patent Number: 5,380,720
[45] Date of Patent: Jan. 10, 1995

[54] IODO VITAMIN $D_3$ COMPOUNDS AND METHOD FOR PREPARING SAME

[75] Inventors: Hector F. DeLuca, Deerfield, Wis.; Rafal R. Sicinski, Pasteura, Poland

[73] Assignee: Wisconsin Alumni Research Foundation, Madison, Wis.

[21] Appl. No.: 60,231

[22] Filed: May 11, 1993

[51] Int. Cl.$^6$ ............................................. C07C 401/00
[52] U.S. Cl. ..................................... 514/167; 552/653
[58] Field of Search .......................... 552/653; 514/167

[56] References Cited

U.S. PATENT DOCUMENTS 5,061,699 10/1991 DeLuca et al. ...................... 514/167
5,182,393 1/1993 Yiannikouros et al. ................. 549/4

FOREIGN PATENT DOCUMENTS 78704 5/1983 European Pat. Off. ... C07D 487/04

Primary Examiner—Howard T. Mars
Assistant Examiner—Kimberly J. Kestler
Attorney, Agent, or Firm—Andrus, Sceales, Starke & Sawall

[57] ABSTRACT

Biologically active 1α-hydroxy-22-iodinated vitamin $D_3$ compounds and a process for the preparation of 1α-hydroxy-22-iodinated vitamin $D_3$ compounds are disclosed. The 22-iodo-vitamin $D_3$ compounds show relatively high binding affinity for the vitamin D receptor demonstrating their potential for high in vivo biological activity. Further, these compounds induce relatively high differentiation of malignant cells. Also, these 22-iodo compounds show high in vivo calcium transport activity with little or no bone calcium mobilization activity. These compounds thus show promise in the treatment of osteoporosis.

28 Claims, 2 Drawing Sheets

IODO VITAMIN D3 COMPOUNDS AND METHOD FOR PREPARING SAME

This invention relates to biologically active vitamin D3 compounds. More specifically, the invention relates to 1α-hydroxylated-22-iodinated vitamin D3 compounds and a process for the preparation thereof.

BACKGROUND AND SUMMARY OF THE INVENTION

The 1α-hydroxylated metabolites of vitamin D—most importantly 1α,25-dihydroxyvitamin D3 and 1α,25-dihydroxyvitamin D2—are known as highly potent regulators of calcium homeostasis in animals and humans, and more recently their activity in cellular differentiation has also been established. V. Ostrem et al, Proc. Natl. Acad. Sci. USA, (1987), 84, 2610. As a consequence, many structural analogs of these metabolites, such as compounds with different side chain structures, different hydroxylation patterns, or different stereochemistry, have been prepared and tested. Important examples of such analogs are 1α-hydroxyvitamin D3, 1α-hydroxyvitamin D2, various side chain fluorinated derivatives of 1α,25-dihydroxyvitamin D3, and side chain homologated analogs. Several of these known compounds exhibit highly potent activity in vivo or in vitro, and some of these have been found to exhibit an interesting separation of activities in cell differentiation and calcium regulation. This difference in activity provides these compounds with advantageous therapeutic activity profiles and thus numerous of these compounds are in use, or have been proposed for use, in the treatment of a variety of diseases such as renal osteodystrophy, vitamin D-resistant rickets, osteoporosis, psoriasis, and certain malignancies.

In a continuing effort to explore pharmacologically important vitamin D analogs, several new 22-iodinated vitamin D3 compounds have now been synthesized. The 22-iodinated compounds show relatively high binding affinity for the vitamin D receptor thus demonstrating their potential for high in vivo biological activity. Further, these compounds induced relatively high differentiation of malignant cells. Also, these 22-iodo compounds showed high in vivo calcium transport activity with little or no bone calcium mobilization activity. Accordingly, the 22-iodo compounds show promise in the treatment of osteoporosis, particularly senile osteoporosis and postmenopausal osteoporosis. The iodo compounds can also be labeled with radio iodine to be used for 1α,25-(OH)2-D3 assays.

DISCLOSURE OF THE INVENTION

Figure 1:
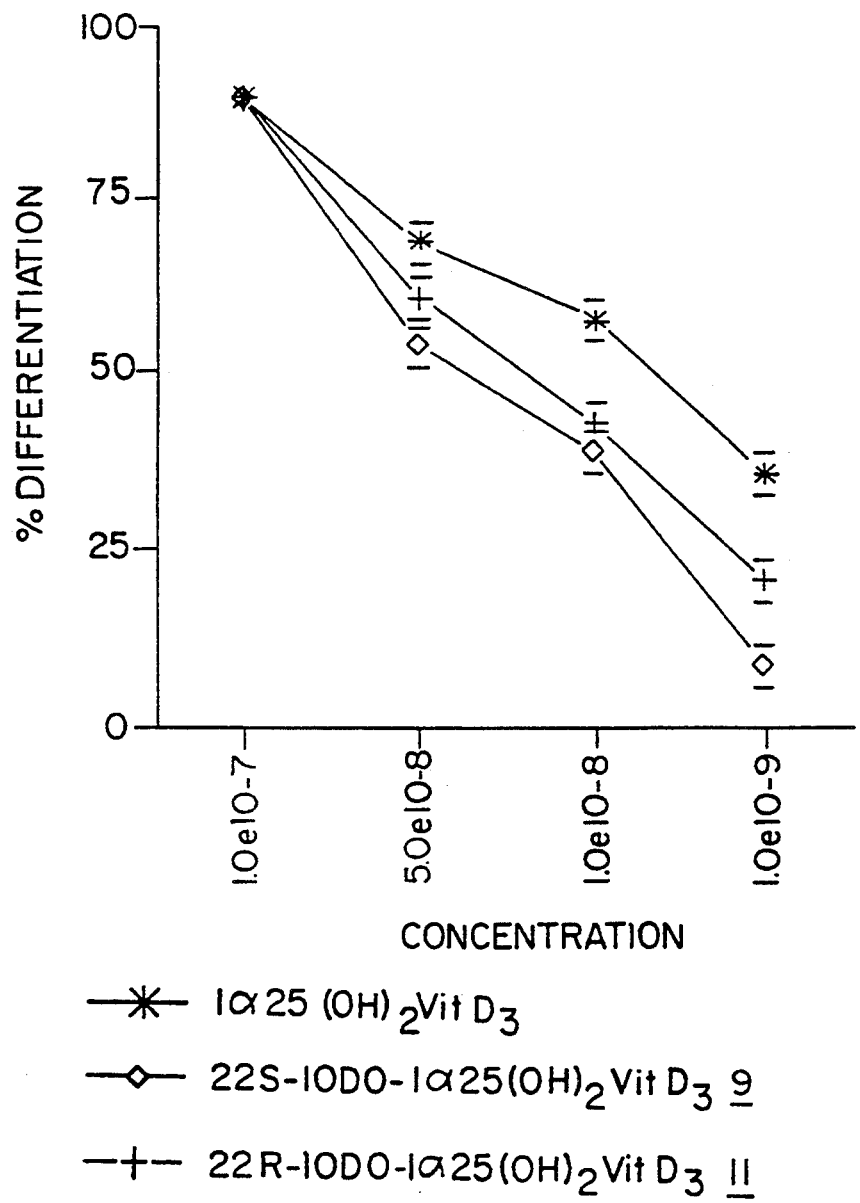
FIG. 1 is a graph of the percent differentiation of HL-60 cells versus concentration for a prior art vitamin D3 compound and two of the new 22-iodo-vitamin D3 compounds.

The present invention is directed to biologically active 1α-hydroxy-22-iodinated vitamin D3 compounds and to a process for the preparation of biologically active 1α-hydroxy-22-iodinated vitamin D3 compounds having the general formulas I and II shown below:

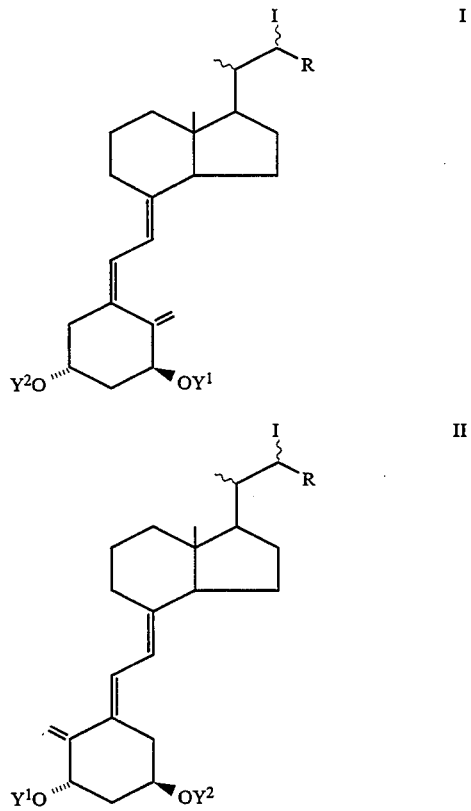

where $Y^1$ and $Y^2$, which may be the same or different, are each selected from the group consisting of hydrogen and a hydroxy-protecting group, and where R is hydrogen, an aryl, alkyl, hydroxyalkyl or fluoroalkyl group, or R may represent the following side chain fragment:

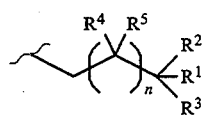

wherein $R^1$ represents hydrogen, hydroxy or protected hydroxy, $R^2$ and $R^3$ are each selected from the group consisting of alkyl, hydroxyalkyl and fluoroalkyl, or, when taken together represent the group —$(CH_2)_m$— where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, and wherein n is an integer having a value of from 1 to 5.

Specific important examples of side chains are the structures represented by formulas (a), (b), (c) and (d) below, i.e. the side chain as it occurs in (22S)-iodo-25-hydroxyvitamin D3 (a); (22S)-iodovitamin D3 (b); (22R)-iodo-25-hydroxyvitamin D3 (c): and (22R)-iodovitamin D3 (d).

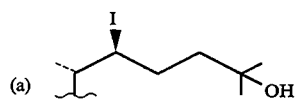

(a)

-continued

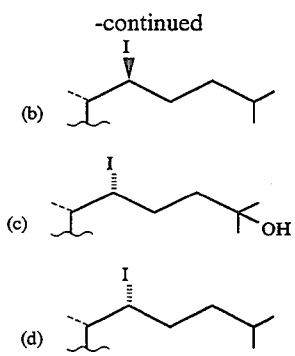

(b)

(c)

(d)

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkyl or arylsilyl radicals, or alkoxyalkyl groups such as methoxymethyl, ethoxymethyl, methoxyethoxyethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl," "fluoroalkyl" and "arylalkyl" refer to such an alkyl radical substituted by one or more hydroxy, fluoro or aryl groups respectively. An "acyl" group is an alkanoyl group of 1 to 6 carbons in all its isomeric forms, or an aroyl group, such as benzoyl, or halo-, nitro- or alkyl-substituted benzoyl groups, or an alkoxycarbonyl group of the type alkyl-O-CO-, such as methoxycarbonyl, ethoxycarbonyl, propyloxycarbonyl, etc., or a dicarboxylic acyl group such as oxalyl, malonyl, succinoyl, glutaroyl, or adipoyl. The term "aryl" signifies a phenyl-, or an alkyl-, nitro- or halo-substituted phenyl group. The term alkoxy signifies the group alkyl-O-.

The wavy lines to the substituents at C-20 (methyl) and C-22 (iodine) indicate that these substituents may have either the R or S configuration.

The preparation of 1α-hydroxy-22-iodovitamin D compounds having the basic structures shown above can be accomplished starting from the diene-protected derivative of structure III or vitamin D compounds of the general structures IV and V

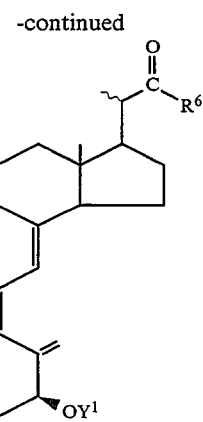

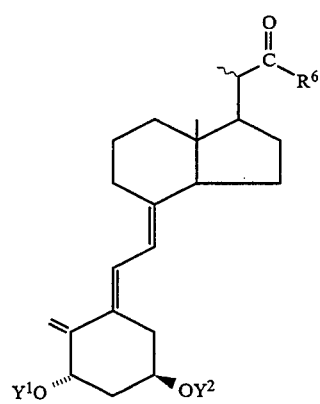

where $Y^1$ and $Y^2$ are as defined above and $R^6$ represents hydrogen, O-alkyl or O-aryl. Reaction of the C-22 aldehydes III, IV or V ($R^6$=hydrogen) with an alkylmagnesium halide having the structure RMgX (R as defined above, X=halogen) or alkyllithium reagent having the structure RLi (R as defined above) in the appropriate inert solvent, provides 22-hydroxy compounds of the general formulas VI, VII and VIII, respectively ($Y^3$=H). Alternatively, the same compounds VI–VIII can be obtained by reaction of the above mentioned organometallic reagents with esters III, IV and V ($R^6$=O-alkyl or O-aryl) under carefully controlled reaction conditions providing 22-ketones of the general formulas III, IV and V ($R^6$=R as defined above) and by subsequent reduction of the 22-oxo group in these compounds by the appropriate reducing agents (e.g. hydride reduction).

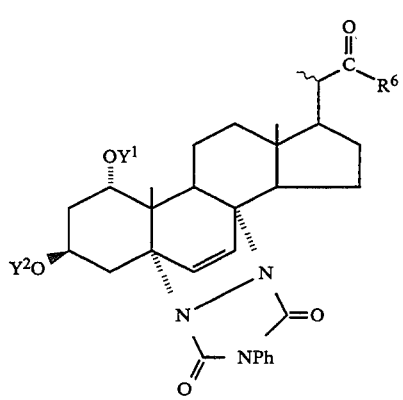

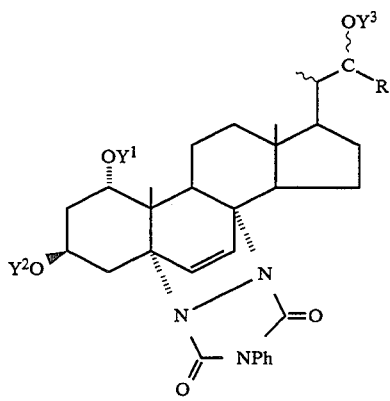

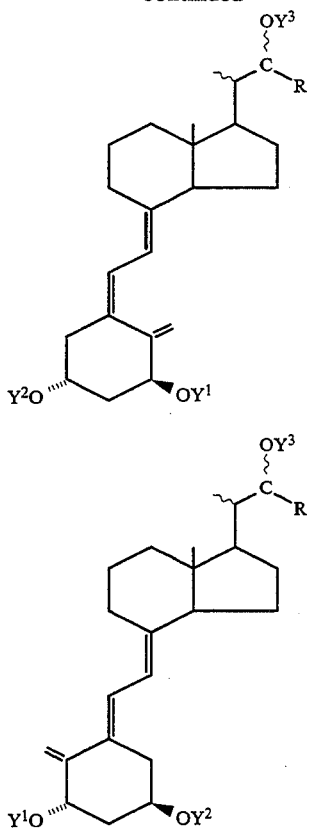

Adduct VI (Y³=H) subjected to basic conditions can be then converted to 5,7-diene steroid which in turn via the well known process consisting of irradiation with UV light and thermal isomerization gives VII (Y³=H).

The 22-hydroxy intermediates VII and VIII (Y³=H) having, preferably, all remaining hydroxy groups protected are then treated with an alkyl- or arylsulfonylhalide (e.g. methanesulfonylchloride, p-toluenesulfonylchloride) in a suitable solvent (e.g. pyridine) to obtain the corresponding 22-O-alkyl- or -arylsulfonyl derivatives (the compounds having the structures shown VII and VIII above, where Y³ is alkyl-$SO_2$- or aryl-$SO_2$-). These sulfonates are then subjected to nucleophilic substitution reaction with a reagent which can serve as an iodine ion source (inorganic iodides e.g. alkali metal iodides, ammonium iodide etc. and organic iodides e.g. tetraalkylammonium iodides etc.) in an appropriate solvent (preferably acetone, 2-butanone, 2-propanol, acetonitrile etc.), at a temperature ranging from 0° C. to the boiling temperature of the solvent, thereby displacing the sulfonate group and obtaining the 22-iodo compounds, represented by the structures I and II above. To avoid undesired isomerization of the 5,6-double bond which can occur due to evolution of small amounts of iodine (radical dissociation of C-I bond) in the reaction medium it is required to perform such substitution reaction in the presence of mercury and in the dark. In order to neutralize strong acids which can be formed in the side processes (concurrent elimination reactions) it is advantageous to add calcium carbonate to the reaction medium.

It is also evident that the reaction of the 22-sulfonates with isotopically labeled iodides (e.g. $NH_4{}^{123}I$, $Na^{125}I$, $Na\ {}^{129}I$, $Na^{131}I$, etc.) provides a convenient means for preparing 22-iodo compounds I and II in isotopically-labeled form. Due to known susceptibility of aliphatic iododerivatives to nucleophilic substitution such radioiodinated compounds can also be prepared by reaction of the unlabeled derivatives I or II with the isotopically labeled iodides (i.e. isotope exchange process). Vitamins of high specific activity (up to 2200 Ci/mmol) labeled with carrier-free radioiodine can be conveniently produced in that manner. These radiolabeled vitamin D derivatives find ready application as tracers in various known binding assays and for other experimental research studies.

The next step of the process comprises the removal of the hydroxy protecting groups to produce the free hydroxy compounds represented by 1α-hydroxyvitamin structures I and II above (where Y¹, Y² and R¹ are hydrogens) or 1α,25-dihydroxyvitamin D structures (where Y¹, Y² are hydrogens and R¹ is hydroxyl). Alternatively, the deprotection of hydroxyl groups may be performed on 22-sulfonates to obtain compounds of structures VII and VIII (where Y³ is alkyl-$SO_2$- or aryl-$SO_2$- and Y¹, Y² and R¹ are hydrogens) which can be then subjected to substitution reaction giving rise to 22-iodo compounds I and II (where Y¹, Y² and R¹ are hydrogens). If obtained as a mixture of the two C22 epimers, 22-alcohols, sulfonates and/or iodides can be separated by chromatographic methods. If desired, the 5,6-cis compounds I, IV and VII can be easily converted to the corresponding 5,6-trans counterparts (and vice versa) II, V and VIII, respectively by the known iodidecatalyzed isomerization process.

This invention is more specifically described by the following illustrative examples. In these examples specific products identified by Arabic numerals (e.g. 1, 2, 3, etc.) refer to the specific structures so identified in the preceding description and in the Schemes.

EXAMPLE 1

Reaction of vitamin D C-22 aldehydes 1 with Grignard reagent derived from bromocompound A (Scheme 1)

A solution of known 4-bromo-2-methyl-2(triethylsiyloxy) butane (A) (94 mg, 0.33 mmol) in anhydrous ether (0.3 mL) was added dropwise to a stirred mixture of magnesium powder (9.7 mg, 0.4 mmol; ~50 mesh, Aldrich) in anhydrous ether (0.2 mL) under argon at room temperature with occasional warming it up to 35° C. After addition was complete the mixture was stirred for 15 min at room temperature and 30 min at 40° C. Then it was cooled to 0° C. and a solution of known C-22 aldehydes (1) [32 mg, 0.056 mmol; see A. Kutner et al., J. Org. Chem. 53, 3450 (1988)] in anhydrous ether (0.3 mL, cooled to 0° C.) was added dropwise. After the reaction mixture was stirred for 20 min at 0° C. and 75 min at room temperature it was quenched with aqueous solution of $NH_4Cl$ (2 mL) and diluted with 4:1 (v/v) benzene/ether (20 mL). The organic layer was separated, washed with water and diluted $NaHCO_3$, dried, and evaporated. TLC and HPLC control indicated formation of only one (22S) of the two possible isomers. Pure (22S)-hydroxyvitamin D derivative (2) was obtained as a colorless oil (31 mg, 72% field) by preparative HPLC (Zorbax-Siliea column 6.2 mm×25 cm) using 3.5% ethyl acetate in hexane as an eluent; peak at 30 mL was collected. UV (EtOH) $\lambda_{max}$ 264 nm, $\lambda_{min}$ 225 nm, $A_{264}/A_{225}=1.6$; ¹H-NMR ($CDCl_3$, 500 MHz): δ0.062 (12 H, br s, 4×SiMe), 0.546 (3 H, s, 18-$H_3$), 0.583 (6 H, q, J=8 Hz, 3×$SiCH_2$), 0.877 (18 H, s, 2×Si-t-Bu), 0.920 (3 H, d, J=6.4 Hz, 21-$H_3$), 0.947 (9 H, t, J=8 Hz, 3×SiCH$_2$CH$_3$), 1.221 and 1.225 (3 H and 3 H, each s, 26- and 27-H$_3$), 2.83 (1 H, br d, J=12.5 Hz, 9β-H), 3.63 (1 H, m, 22-H), 4.19 (1 H, m, 3α-H), 4.37 (1 H, m, 1β-H), 4.87 and 5.18 (1 H and 1 H, each s, 19-H$_2$), 6.02 (1 H, d, J=11.2 Hz, 7-H), 6.24 (1 H, d, J=11.2 Hz, 6-H); MS, m/z (rel intensity) 774 (M+, 15), 642 (43), 75 (100); exact mass calcd for C$_{45}$H$_{86}$O$_4$Si$_3$ 774.5834, found 774.5850.

EXAMPLE 2

Reaction of 22-hydroxyvitamin D compound (2) with p-toluenesulfonyl chloride

To a solution of alcohol (2) (28 mg, 0.036 mmol) in dry pyridide (100 μL) was added fleshly recrystallized p-toluenesulfonyl chloride and the reaction was allowed to proceed for 64 h at 4° C. The reaction mixture was poured into ice/saturated NaHCO$_3$ with stirring. After 40 min of stirring the aqueous suspension was extracted with 4:1 (v/v) benzene/ether (3×10 mL). The combined organic extracts were washed with saturated NaHCO$_3$, water, saturated CuSO$_4$, again water, dried (Na$_2$SO$_4$) and evaporated. The oily yellowish residue was purified by preparative HPLC (Zorbax-Silica column 6.2 mm×25 cm) using 2% ethyl acetate in hexane as an eluent. Pure tosylate (3) (26 rag, 78%; collected at 20 mL) was obtained as a colorless oil: UV (hexane) λ$_{max}$ 264 and 223 nm, λ$_{min}$ 238 nm; $^1$H-NMR (CDCl$_3$, 500 MHz): δ0.059 and 0.067 (6 H and 6 H, each s, 2×SiMe$_2$), 0.479 (3 H, s, 18-H$_3$), 0.528 (6 H,q, J=8 Hz, 3×SiCH$_2$), 0.877 (18 H, s, 2×Si-t-Bu), 0.915 (9 H, t, J=8 Hz, 3×SiCH$_2$CH$_3$), 0.929 (3 H, d, J=6.0 Hz, 21-H$_3$), 1.103 and 1.141 (3 H and 3 H, each s, 26- and 27-H$_3$), 2.43 (3 H, s, ArMe), 2.80 (1 H, br d, J=12.3 Hz, 9β-H), 4.19 (1 H, m, 3α-H), 4.38 (1 H, m, 1β-H), 4.58 (1 H, t, J=7.1 Hz, 22-H), 4.86 and 5.19 (1 H and 1 H, each s, 19-H$_2$), 5.99 (1 H, d, J=11.2 Hz, 7-H), 6.22 (1 H, d, J=11.2 Hz, 6-H), 7.32 (2 H, d, J=8 Hz, ArH), 7.80 (2 H, d, J=8 Hz, Ar-H); MS, m/z (rel intensity) 928 (M+, 1), 796 (2), 756 (3), 664 (3), 624 (47), 492 (27), 173 (100); exact mass calcd for C$_{52}$H$_{92}$O$_6$Si$_3$S 928.5922, found 928.5894.

EXAMPLE 3

Reaction of vitamin D 22-p-toluenesulfonate (3) with sodium iodide

To a stirred solution of tosylate (3) (4.6 mg, 5 μmol) in 1:1 (v/v) acetone/2-butanone (200 μL) was added a drop of mercury (220 mg) and anhydrous calcium carbonate (1 mg, 10 μmol) followed by sodium iodide (3.7 mg, 25 μmol). The resultant mixture was stirred and heated for 100 h at 45° C. in the dark under argon, by which time almost no starting material remained. The reaction mixture was poured into water (10 mL) and extracted with ethyl acetate (2×10 mL). The combined organic layers were washed with 1% Na$_2$S$_2$O$_3$ and water, dried (Na$_2$SO$_4$) and evaporated. The work up of the reaction mixture and following chromatographic separations were done using subdued light in the laboratory and exposure of products to any light, particularly of wavelength close to the carbon-iodine bond absorption (259 nm) was avoided as much as possible. The mixture of products was then repeatedly chromatographed by HPLC (6.2 mm×25 cm Zorbax-Silica column) using 0.1% ethyl acetate in hexane as an eluent. The peaks of 22S-iodocompound (4) and 22R-isomer (5) partially overlapped (R$_v$'s 48 mL and 53 mL, respectively) but rechromatography (or recycling of both peaks) afforded pure material.

(22S)-iodocompound (4) (0.8 mg, 18%): UV (hexane) λ$_{max}$ 264 nm, λ$_{min}$ 227 nm; A$_{264}$/A$_{227}$=1.6; $^1$H-NMR (CDCl$_3$, 500 MHz) δ 0.058 and 0.064 (6 H and 6 H, each s, 2×SiMe$_2$), 0.569 (6 H, q, J=8 Hz, 3×SiCH$_2$), 0.597 (3 H, s, 18-H$_3$), 0.875 (18 H, br s, 2×Si-t-Bu), 0.944 (9 H, t, J=8 Hz, 3×SiCH$_2$CH$_3$), 0.964 (3 H, d, J=6 Hz, 21-H$_3$), 1.194 and 1.211 (3H and 3H, each s, 26- and 27-H$_3$), 2.82 (1 H, br d, J~13 Hz, 9β-H), 4.19 (2 H, m, 3α- and 22-H), 4.37 (1 H, m, 1β-H), 4.86 and 5.18 (1 H and 1 H, each s, 19-H$_2$), 6.02 (1 H, d, J=11.2 Hz, 7-H), 6.23 (1 H, d, J=11.2 Hz, 6-H); MS, m/z (rel intensity) 884 (M+, 21), 752 (62), 624 (22), 248 (100); exact mass calcd for C$_{45}$H$_{85}$O$_3$Si$_3$I 884.4851, found 884.4875.

(22R)-iodocompound (5) (0.4 mg, 9%): UV (hexane)) λmax 264 nm, λ$_{min}$ 227 nm;A$_{264}$/A$_{227}$=1.8; $^1$H-NMR δ 0.064 (12 H, br s, 4×SiMe), 0.517 (3 H, s, 18-H$_3$), 0.568 (6 H, q, J=8 Hz. 3×SiCH$_2$), 0.875 (18 H, br s, 2×Si-t-Bu), 0.950 (9 H, t, J=8 Hz, 3×SiCH$_2$CH$_3$), 1.158 (3 H, d, J=6.8 Hz, 21-H$_3$), 1.179 (6 H, br s, 26- and 27-H$_3$), 2.83 (1 H, br d, J~13 Hz, 9β-H), 4.19 (1 H, m, 3α-H), 4.37 (1 H, m, 1β-H), 4.45 (1 H, d, J=11 Hz, 22-H), 4.86 and 5.18 (1 H and 1 H, each s, 19-H$_2$), 6.02 (1 H, d, J=11.2 Hz, 7-H), 6.23 (1 H, d, J=11.2 Hz, 6-H); MS, m/z (rel intensity) 884 (M+, 20), 752 (54), 624 (24), 248 (100); exact mass calcd for C$_{45}$H$_{85}$O$_3$Si$_3$I 884.9851, found 884.4899. Both iodovitamins (4) and (5), when protected from light can be stored for a prolonged time in a freezer with neither 5,6-cis/trans isomerization nor epimerization at C-22. If desired, however, both processes can be easily performed. In order to achieve the interconversion between both C(22)-epimers each compound (4) and (5) can be subjected to an analogous nucleophilic substitution reaction with NaI as described above for the tosylate (3). In both cases the similar equilibrium mixture can be obtained consisting of epimeric (22S)- and (22R)-iodocompounds (4) and (5) in a ratio of about 3–4:1. Transformation of 5,6-cis isomers to their 5,6-trans analogs is described in the following Example.

EXAMPLE 4

5,6-Double bond isomerization of 22-iodovitamin D compounds (4) and (5)

The synthetic process described in the Example 3 above ensures the preparation of pure 5,6-cis isomers (4) and (5) uncontaminated by 5,6-trans counterparts. Such geometrical isomers are easily distinguishable by both chromatographical and spectral properties. If required, iodine-catalyzed isomerization of 5,6-cis compounds (4) and (5) to the respective 5,6-trans products (6) and (7) can be accomplished according to a known procedure [see A. Verloop et al., Rec. Trav. Chim. Pays-Bas 78, 1004 (1959)]. Thus, treatment of compound (4) in ether with a catalytic amount of iodine [2% of the amount of (4)], while keeping the solution under diffuse daylight for 1h, results in cis to trans isomerization and after HPLC separation (Zorbax-Silica column 6.2 mm×25 cm, 0.1% ethyl acetate in hexane), the 5,6-trans isomer (6) is obtained (R$_v$ 60 mL). Similarly, compound (5), upon treatment with iodine under the above conditions, is isomerized to (7), which can be obtained in pure form after HPLC (conditions as above) separation (R$_v$ 70 mL).

(6). $^1$H-NMR (CDCl$_3$, 500 MHz) δ0.609 (3 H, s, 18-H$_3$), 0.967 (3 H, d, J=6 Hz, 21-H$_3$), 1.201 and 1.216 (3

H and 3 H, each s, 26- and 27-$H_3$), 2.88 (1 H, br d, J~13 Hz, 9β-H), ca 4.2 (2 H, m, 3α- and 22-H), 4.57 (1 H, m, 1β-H), 4.95 and 4.99 (1 H and 1 H, each s, 19-$H_2$), 5.83 and 6.47 (1 H and 1 H, each d, J=11 Hz, 7- and 6-H).

(7). $^1$H-NMR (CDCl$_3$, 500 MHz) δ0.532 (3 H, s, 18-$H_3$), 1.167 (3 H, d, J=6 Hz, 21-$H_3$), 1.185 (6 H, br s, 26- and 27-$H_3$), 2.88 (1 H, br d, J~13 Hz, 9β-H), 4.22 (1 H, m, 3α-H), 4.46 (1 H, d, J=11 Hz, 22-H), 4.54 (1 H, m, 1β-H), 4.95 and 4.99 (1 H and 1 H, each s, 19-$H_2$), 5.83 and 6.46 (1 H and 1H, each d, J=11 Hz, 7- and 6-H).

EXAMPLE 5

Deprotection of hydroxyl groups in 22-iodovitamin D compounds (4) and (5)

Each of 22-iodovitamins was separately hydrolyzed using the same procedure. To a solution of protected triol (4) (1 mg) in anhydrous benzene (50 μL) was added AG 50W-X4 ion exchange resin (20 mg, prewashed with methanol) as a slurry in an anhydrous methanol (200 μL). A drop of mercury (400 mg) was added and the resultant mixture was vigorously stirred at room temperature for 10 h in the dark under argon. The reaction was diluted with 1:1 (v/v) ether/ethyl acetate (1 mL), the solution was decanted and transferred to a separatory funnel and the resin was washed with 1:1 ether/ethyl acetate (2×2 mL). The combined organic phase was washed with 5 mL portions of brine, 1% Na$_2$S$_2$O$_3$, saturated NaHCO$_3$, and brine again, dried (Na$_2$SO$_4$) and evaporated (temp. below 35° C.). The work up of the reaction mixture and following chromatographic separations were done using subdued light in the laboratory and exposure of iodinated compounds to any light, particularly of wavelength close to the carbon-iodine absorption (259 nm), was avoided as much as possible. Preparative HPLC [6.2 mm×25 cm Zorbax-Silica column, 1:1 (v/v) hexane/ethyl acetate as an eluent] provided small amount of (22R, 25)-epoxy-1α-hydroxyvitamin D$_3$ (8) (eluted at R$_v$ 34 mL). Further elution gave (22S)-iodo-1α,25-dihydroxyvitamin D$_3$ (9):

R$_v$ 79 mL; UV (EtOH) λ$_{max}$ 264 nm, λ$_{min}$ 227 nm, A$_{264}$/A$_{227}$=2.0; $^1$H-NMR (CDCl$_3$, 500 MHz) δ 0.607 (3 H, s, 18-$H_3$), 0.975 (3 H, d, J=5.9 Hz, 21-$H_3$), 1.23 and 1.24 (3 H and 3 H, each s, 26- and 27-$H_3$), 2.83 (1 H, br d, J~13 Hz, 9β-H), 4.21 (2 H, m, 3α- and 22-H), 4.44 (1 H, m, 1β-H), 5.00 and 5.33 (1 H and 1 H, each s, 19-$H_2$), 6.02 (1 H, d, J=11.3 Hz, 7-H), 6.38 (1 H, d, J=11.3 Hz, 6-H); MS, m/z (rel intensity) 542 (M$^+$, 2), 524 (M$^+$- H$_2$O, 31), 506 (M$^+$- 2H$_2$O, 17), 414 (M$^+$- HI, 8), 396 (M$^+$- HI - H$_2$O, 54), 378 (M$^+$- HI - 2 H$_2$O, 21), 99 (100); exact mass calcd for C$_{27}$H$_{41}$O$_2$I (M$^+$- H$_2$O) 524.215 1, found 524.2145.

Analogously performed hydrolysis of 22-iodocompound (5) gave after HPLC separation (conditions as above) a trace of (22S,25)-epoxy-1α-hydroxyvitamin D$_3$ (8) (eluted at R$_v$ 28 mL) and (22R)-iodo-1α,25-dihydroxyvitamin D$_3$ (11): R$_v$ 63 mL; UV (EtOH) λ$_{max}$ 264 nm, λ$_{min}$ 228 nm, A$_{264}$/A$_{228}$=1.7; $^1$H-NMR (CDCl$_3$, 500 MHz) δ0.535 (3 H, s, 18-$H_3$), 1.172 (3 H, d, J=6.5 Hz, 21-$H_3$), 1.224 (6 H, br s, 26- and 27-$H_3$), 2.82 (1 H, br d, J~13 Hz, 9β-H), 4.24 (1 H, m, 3α-H), 4.45 (1 H, m, 1β-H), 4.47 (1 H, d, J=12 Hz, 22-H), 5.00 and 5.33 (1 H and 1 H, each s, 19-$H_2$), 6.02 (1 H, d, J=11.2 Hz, 7-H), 6.37 (1 H, d, J=11.2 Hz, 6-H); MS m/z (rel intensity) 542 (M$^+$, 8), 524 (M$^+$- H$_2$O, 64), 506 (M$^+$- 2 H$_2$O, 19), 414(M$^+$- HI, 10), 396 (M$^+$- HI - H$_2$O, 62), 378 (M$^+$- HI - 2 H$_2$O, 9), 99 (100); exact mass calcd for C$_{27}$H$_{43}$O$_3$I 542.2257, found 542.2248; calcd for C$_{27}$H$_{41}$O$_2$I (M$^+$- H$_2$O) 524.2151, found 524.2136.

Elongation of the hydrolysis time results in the formation of increasing proportions of cyclic ethers (8) or (10). These conversions are useful for correlating the respective C(22)-epimeric iodocompounds with starting tosylates. Thus, for example, (22S)-tosylate (3) subjected to the analogous (mercury is not necessary) hydrolysis conditions as described above formed (22R, 25)-epoxy-1α-OH-D$_3$ 8 (63% yield) as the only isolable product.

SCHEME 1

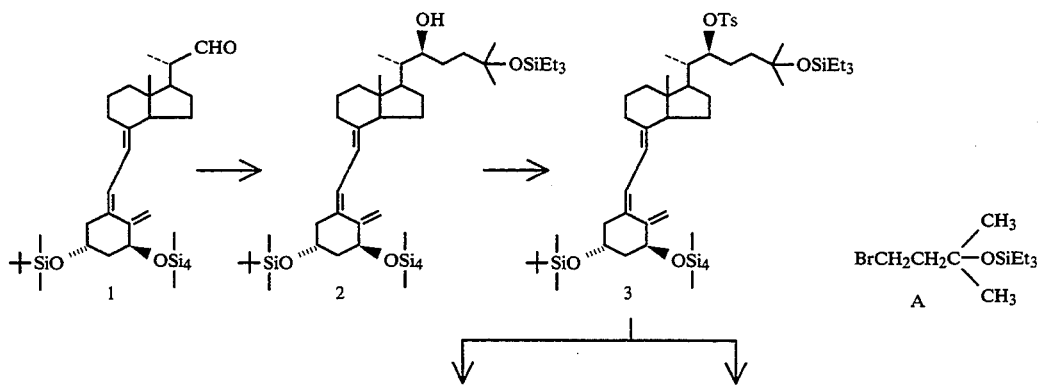

-continued
SCHEME 1

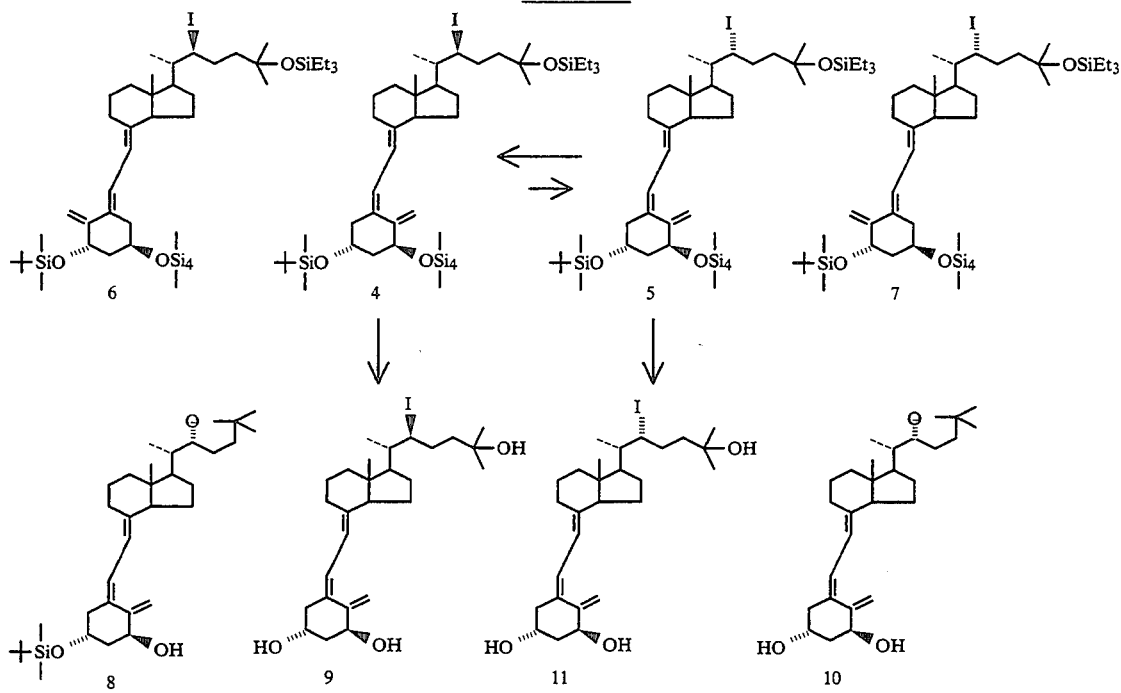

Biological Activity of 1α-Hydroxy-22-Iodo-Vitamin D Compounds

The novel compounds of this invention exhibit an unexpected pattern of biological activity. All of the 22-iodo compounds exhibited high potency in promoting the differentiation of malignant cells. Competitive binding tests also showed that these compounds have the potential for high in vivo biological activity. In addition, the 22-iodo compounds showed high in vivo calcium transport activity with little or no bone calcium mobilization activity. This is illustrated by the biological assay results obtained for the claimed 22-iodo-vitamin $D_3$ compounds, which are summarized in FIGS. 1 and 2, and Table 1. FIG. 1 shows a comparison of the activity of the known active metabolite 1α,25-dihydroxyvitamin $D_3$ and two of the 22-iodo analogs in inducing the differentiation of human leukemia cells (HL-60 cells) in culture to normal cells (monocytes). Differentiation activity was assessed by a standard differentiation assay, abbreviated in FIG. 1 as NBT (nitroblue tetrazolium reduction). The assay was conducted according to known procedures, as given, for example, by DeLuca et al U.S. Pat. No. 4,717,721 and Ostrem et al, J. Biol. Chem. 262, 14164, 1987. For the assay, the differentiation activity of the test compounds is expressed in terms of the percent of HL-60 cells having differentiated to monocytes in response to a given concentration of test compound.

The results summarized in FIG. 1 clearly show that the new 22-iodo-vitamin $D_3$ analogs and specifically (22S)-iodo-1α,25-dihydroxyvitamin $D_3$ and (22R)-iodo-1α,25-dihydroxyvitamin $D_3$, are as potent as 1α,25-dihydroxyvitamin $D_3$ in promoting the differentiation of leukemia cells. Thus in NBT assay close to 90% of the cells are induced to differentiation by 1α,25-dihydroxyvitamin $D_3$ at a concentration of $1 \times 10^{-7}$ molar, and the same degree of differentiation is achieved by the two 22-iodo analogs.

Figure 2:
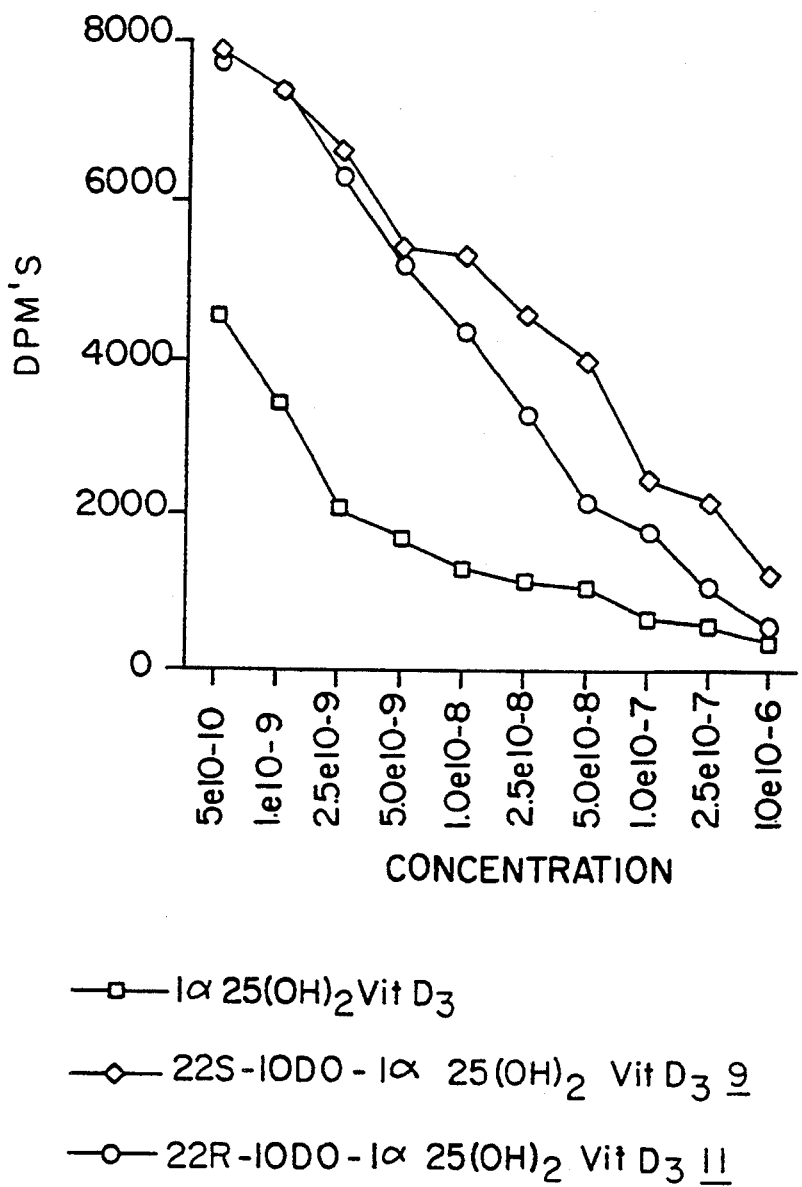
FIG. 2 is a graph of the competitive binding ability versus concentration for the same three compounds as in FIG. 1.

FIG. 2 shows a comparison of the same three compounds as in FIG. 1 illustrating their relative activity with regard to competitive binding to the vitamin D receptor. The competitive receptor binding was done with pig nuclear extract (PNE) as described in Perlman et al. Biochemistry 29, 190–196 (1990) using the porcine extract prepared as described by Dame et al PNAS 82, 7825–7829 (1985). These data are used to demonstrate that the 22-iodo compounds, and in particular the 22S (compound 9) and 22R (compound 11) analogs tested, have potential for high in vivo biological activity.

In regard to the biological data on the calcemic activity of these compounds reported in Table 1, the data in Table 1 illustrate that (22S)-iodo-1α,25-dihydroxyvitamin $D_3$ has biological activity in intestinal calcium transport much higher, i.e. about double, to that of 1,25-$(OH)_2D_3$. The data also illustrates that this compound possesses little or no bone calcium mobilizing activity even when given at 1 μg per day for six days.

The 22-iodo compounds would thus find utility as a treatment for osteoporosis, particularly postmenopausal osteoporosis and senile osteoporosis. The utility for these compounds results from their low bone calcium mobilizing activity with normal differentiative activity, normal binding to the receptor, and high calcium transport activity.

TABLE 1

INTESTINAL CALCIUM TRANSPORT AND BONE CALCIUM MOBILIZATION ACTIVITY OF 22S-IODO-1,25-$(OH)_2D_3$

| Compound | Dose (μg/d/ 6 days) | Intestinal Calcium Transport (Serosal/Mucosal Ratio) | Bone Calcium Mobilization (Serum Calcium) (mg/100 ml) |
|---|---|---|---|
| None (-D) | 0 | 4.0 ± 0.2 | 4.1 ± 0.1 |
| 1,25-$(OH)_2D_3$ | 0.1 | 11.2 ± 1.2 | 5.9 ± 0.3 |
| 22S-Iodo- | 1.0 | 22.8 ± 1.4 | 4.9 ± 0.1 |

TABLE 1-continued
INTESTINAL CALCIUM TRANSPORT AND BONE CALCIUM MOBILIZATION ACTIVITY OF 22S-IODO-1,25-(OH)$_2$D$_3$

| Compound | Dose (μg/d/ 6 days) | Intestinal Calcium Transport (Serosal/Mucosal Ratio) | Bone Calcium Mobilization (Serum Calcium) (mg/100 ml) |
|---|---|---|---|
| 1,25-(OH)$_2$D$_3$ | | | |

Rats were fed the vitamin D-deficient, low calcium (0.02%) diet for 3 weeks and then given the indicated dose in 0.1 ml propylene glycol:ethanol (95:5) intraperitoneally each day for 6 days. On day 7, serum was analyzed for calcium and the duodenum used to measure intestinal calcium transport as described by Martin et al. Am. J. Physiol. 216, 1351–1359, 1969, as modified by Perlman et al. Biochemistry, 29, 190–196, 1990.

For treatment purposes, the novel compounds of this invention can be formulated as solutions in innocuous solvents, or as emulsions, suspensions or dispersions in suitable innocuous solvents or carriers, or as pills, tablets or capsules, containing solid carriers according to conventional methods known in the art. For topical applications the compounds are advantageously formulated as creams or ointments or similar vehicle suitable for topical applications. Any such formulations may also contain other pharmaceutically-acceptable and non-toxic excipients such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal, or topically in the form of ointments, lotions, or in suitable transdermal patches. For the treatment of malignant diseases, the 22-iodo-vitamin D compounds of this invention are administered to subjects in dosages sufficient to inhibit the proliferation of malignant cells and induce their differentiation into normal monocyte-macrophages. Suitable dosage amounts are from 0.5 to 500 μg of compound per day, such dosages being adjusted, depending on the disease to be treated, its severity and the response or condition of the subject as is well-understood in the art.

We claim:

1. Vitamin D compounds having the structure I and II shown below:

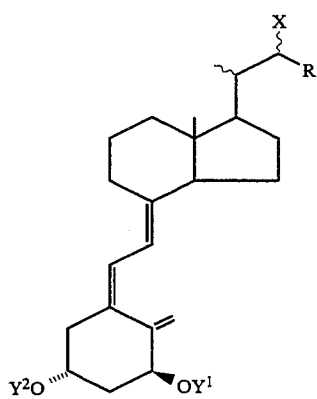

I

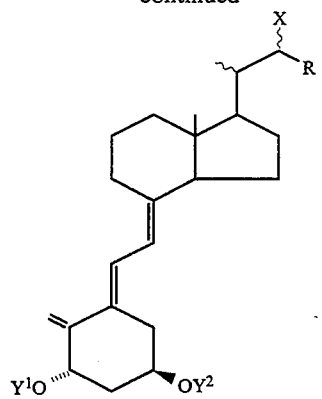

II where X is iodine, $Y^1$ and $Y^2$, which may be the same or different, are each selected from the group consisting of hydrogen and a hydroxy-protecting group, and where R is an aryl, alkyl, hydroxyalkyl or fluoroalkyl group, or R may represent the following side chain fragment:

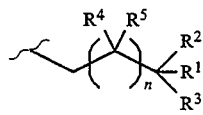

wherein $R^1$ represents hydrogen, hydroxy or protected hydroxy, $R^2$ and $R^3$ are each selected from the group consisting of alkyl, hydroxyalkyl and fluoroalkyl, or, when taken together represent the group —(CH$_2$)$_m$— where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, and wherein n is an integer having a value of from 1 to 5.

2. A pharmaceutical composition comprising a 22-iodo-vitamin D compound as defined in claim 1 together with a pharmaceutically acceptable excipient.

3. The pharmaceutical composition of claim 2 wherein said 22-iodo-vitamin D compound is 22S-iodo-vitamin D$_3$.

4. The pharmaceutical composition of claim 2 wherein said 22-iodo-vitamin D compound is 22S-iodo-25-hydroxyvitamin D$_3$.

5. The pharmaceutical composition of claim 2 wherein said 22-iodo-vitamin D compound is 22S-iodo-1α-hydroxyvitamin D$_3$.

6. The pharmaceutical composition of claim 2 wherein said 22-iodo-vitamin D compound is 22S-iodo-1α,25-dihydroxyvitamin D$_3$.

7. The pharmaceutical composition of claim 2 wherein said 22-iodo-vitamin D compound is 22R-iodo-vitamin D$_3$.

8. The pharmaceutical composition of claim 2 wherein said 22-iodo-vitamin D compound is 22R-iodo-25hydroxyvitamin D$_3$.

9. The pharmaceutical composition of claim 2 wherein said 22-iodo-vitamin D compound is 22R-iodo-1α-hydroxyvitamin D$_3$.

10. The pharmaceutical composition of claim 2 wherein said 22-iodo-vitamin D compound is 22R-iodo-1α,25-dihydroxyvitamin D$_3$.

11. A method of treating osteoporosis comprising administering to a patient an effective amount of a 22-iodo-vitamin $D_3$ compound having the structure I and II shown below:

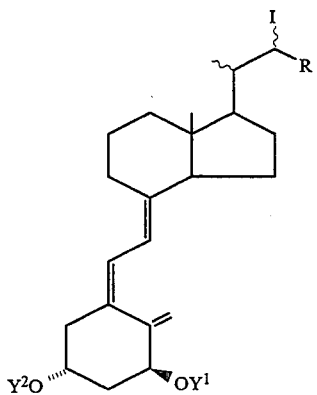

I

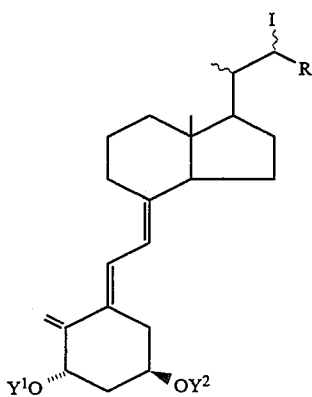

II where $Y^1$ and $Y^2$, which may be the same or different, are each selected from the group consisting of hydrogen and a hydroxy-protecting group, and where R is hydrogen, an aryl, alkyl, hydroxyalkyl or fluoroalkyl group, or R may represent the following side chain fragment:

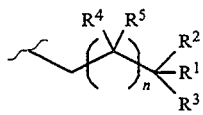

wherein $R^1$ represents hydrogen, hydroxy or protected hydroxy, $R^2$ and $R^3$ are each selected from the group consisting of alkyl, hydroxyalkyl and fluoroalkyl, or, when taken together represent the group—$(CH_2)_m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, and wherein n is an integer having a value of from 1 to 5.

12. The method of claim 11 wherein the 22-iodo-vitamin $D_3$ compound is administered in an amount of from about 0.5 μg to about 500 μg per day.

13. The method of claim 11 wherein the osteoporosis is senile osteoporosis.

14. The method of claim 11 wherein the osteoporosis is postmenopausal osteoporosis.

15. The method of claim 14 wherein the 22-iodo-vitamin $D_3$ compound is administered to women during and subsequent to menopause.

16. The method of claim 14 wherein the 22-iodo-vitamin $D_3$ compound is administered to women prior to the onset of menopause.

17. The method of claim 11 wherein he osteoporosis is low bone turnover osteoporosis.

18. The method of claim 11 wherein the 22-iodo-compound, in solution in a liquid vehicle ingestible by and nontoxic to said patient, is administered orally in encapsulated form.

19. The method of claim 11 wherein the 22-iodo-vitamin $D_3$ compound is administered in a slow release formulation.

20. The method of claim 11 wherein the 22-iodo-vitamin $D_3$ compound is administered daily in divided dosages.

21. 22S-iodo-vitamin $D_3$.
22. 22S-iodo-25-hydroxyvitamin $D_3$.
23. 22S-iodo-1α-hydroxyvitamin $D_3$.
24. 22S-iodo- 1α,25-dihydroxyvitamin $D_3$.
25. 22R-iodo-vitamin $D_3$.
26. 22R-iodo-25-hydroxyvitamin $D_3$.
27. 22R-iodo- 1α-hydroxyvitamin $D_3$.
28. 22R-iodo-1α,25-dihydroxyvitamin $D_3$.

* * * * *